United States Patent [19]
Livneh

[11] Patent Number: 5,718,714
[45] Date of Patent: Feb. 17, 1998

[54] SURGICAL INSTRUMENT WITH REMOVABLE SHAFT ASSEMBLY

[75] Inventor: Steve Livneh, Windsor, Canada

[73] Assignee: Circon Corporation, Santa Barbara, Calif.

[21] Appl. No.: 320,449

[22] Filed: Oct. 11, 1994

[51] Int. Cl.⁶ .......................... A61B 17/32; A61B 17/28; A61B 17/00
[52] U.S. Cl. .............................. 606/205; 606/174; 606/1
[58] Field of Search ................... 606/1, 205–209, 606/139–150, 167, 170, 171, 169, 180, 174, 110, 113, 45–50; 128/749–754

[56] References Cited

U.S. PATENT DOCUMENTS

| | | | |
|---|---|---|---|
| 5,282,800 | 2/1994 | Foshee et al. | 606/205 |
| 5,368,606 | 11/1994 | Marlow et al. | 606/170 |
| 5,395,364 | 3/1995 | Anderhub et al. | 606/205 |
| 5,496,347 | 3/1996 | Hashiguchi et al. | 606/205 |
| 5,507,774 | 4/1996 | Holmes et al. | 606/205 |
| 5,527,339 | 6/1996 | Koscher et al. | 606/205 |

*Primary Examiner*—Glenn K. Dawson
*Attorney, Agent, or Firm*—Daniel J. Meaney, Jr.

[57] ABSTRACT

A surgical instrument having a removable shaft assembly and a handle mechanism is shown. The surgical instrument shaft assembly includes a drive shaft having an actuatable working member at one end and a connecting member at its other end. The drive shaft has formed thereon a reaction member having a preselected geometrical shape. The reaction member is adapted to removeably operatively connect with a receiving member forming a reacting support. A driving force applied to the drive shaft reacts with the reacting support developing a reaction force to actuate the actuatable working member in a predetermined direction. The surgical instrument further includes a handle assembly which for removeably supporting the shaft assembly. The handle assembly has a first end which defines a receiving member to removeably operatively connect with the reaction member to define the reaction support. The handle assembly includes a releasable coupling member which releasably connects with the connecting member. A rotary member is provided which permits rotation of the elongated housing, shaft assembly and actuatable working member. A locking member is provided to inhibit rotation of the drive shaft when the actuatable working member is actuated.

47 Claims, 7 Drawing Sheets

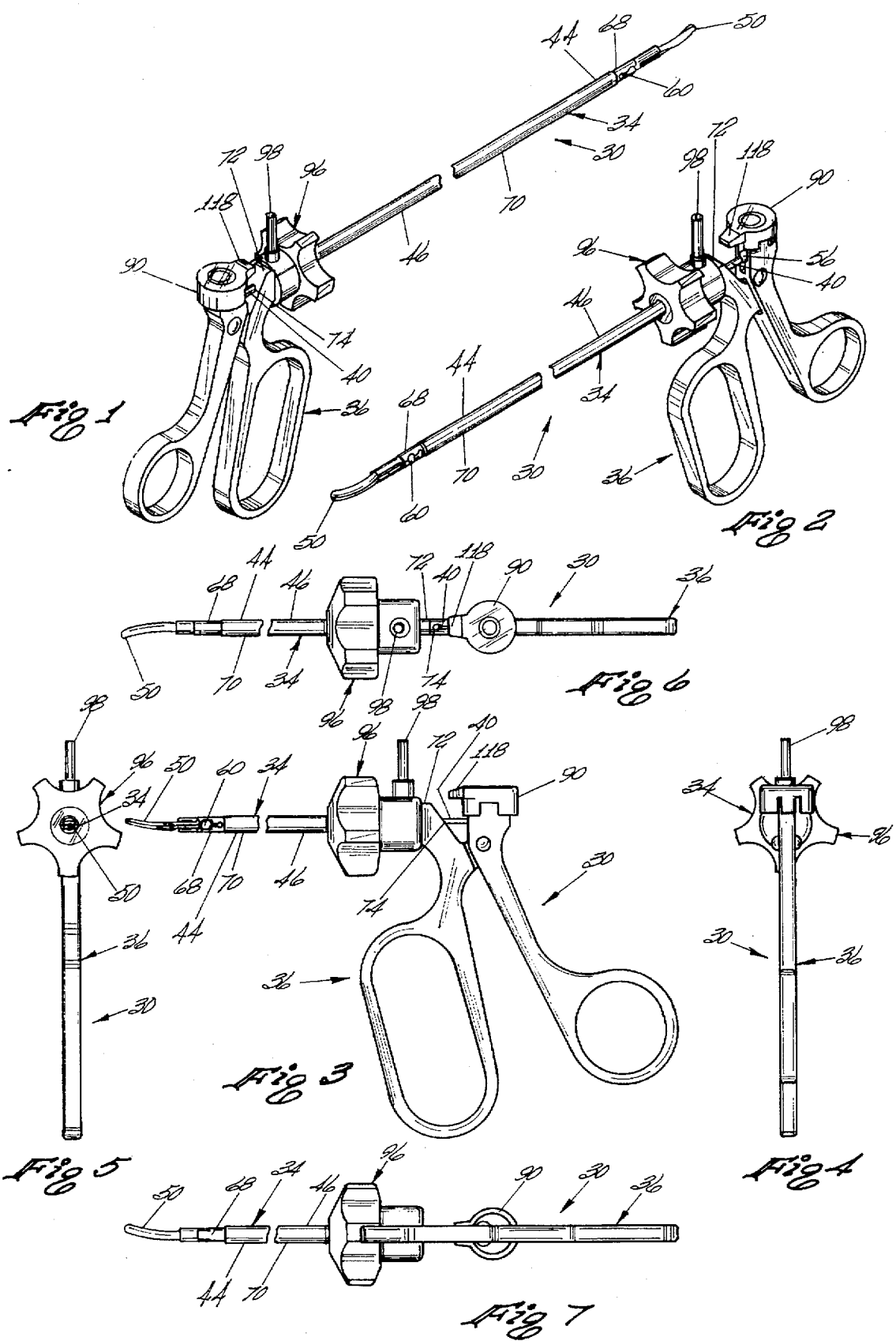

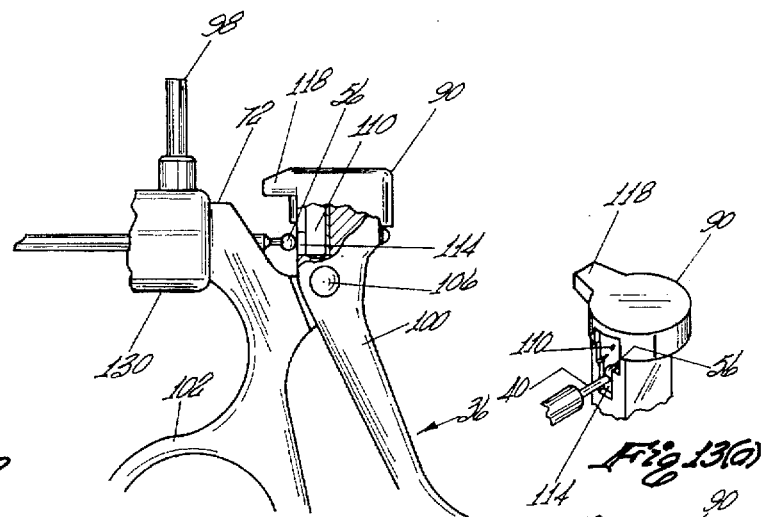
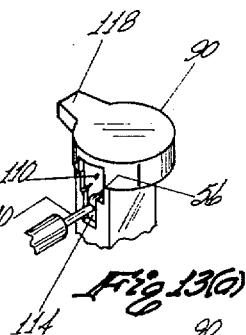
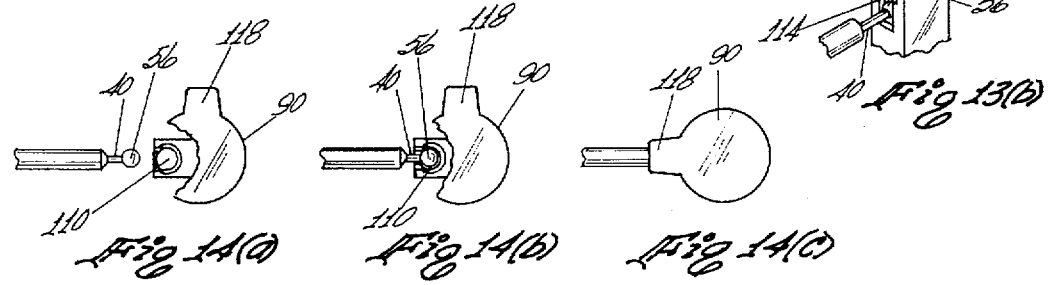
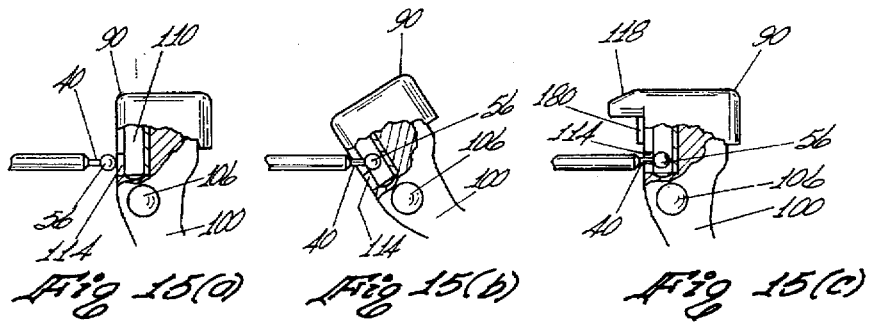
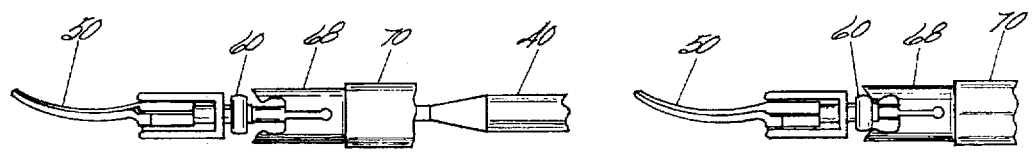
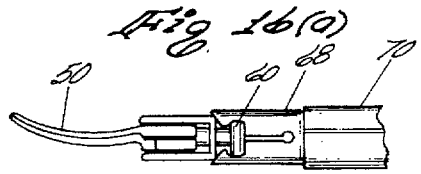

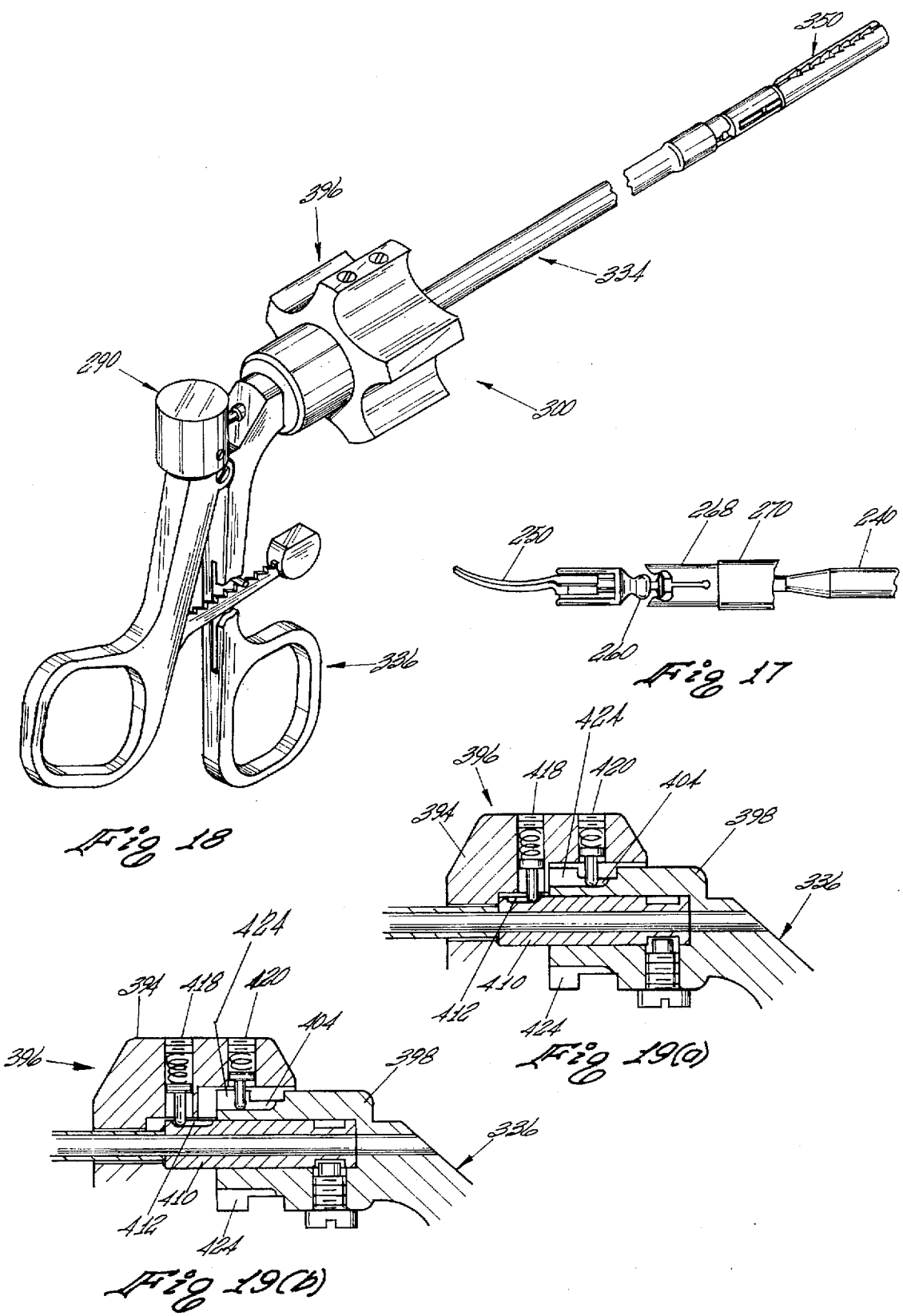

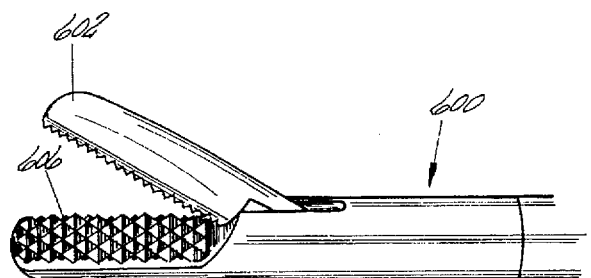
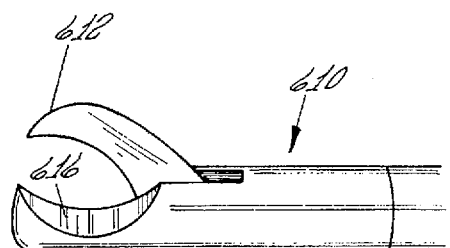
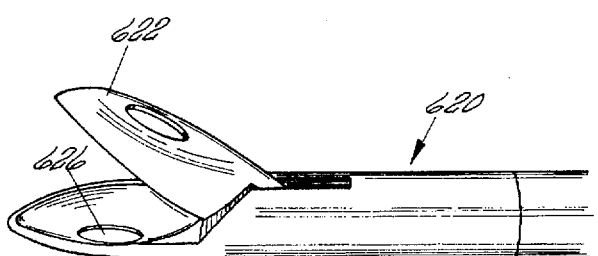
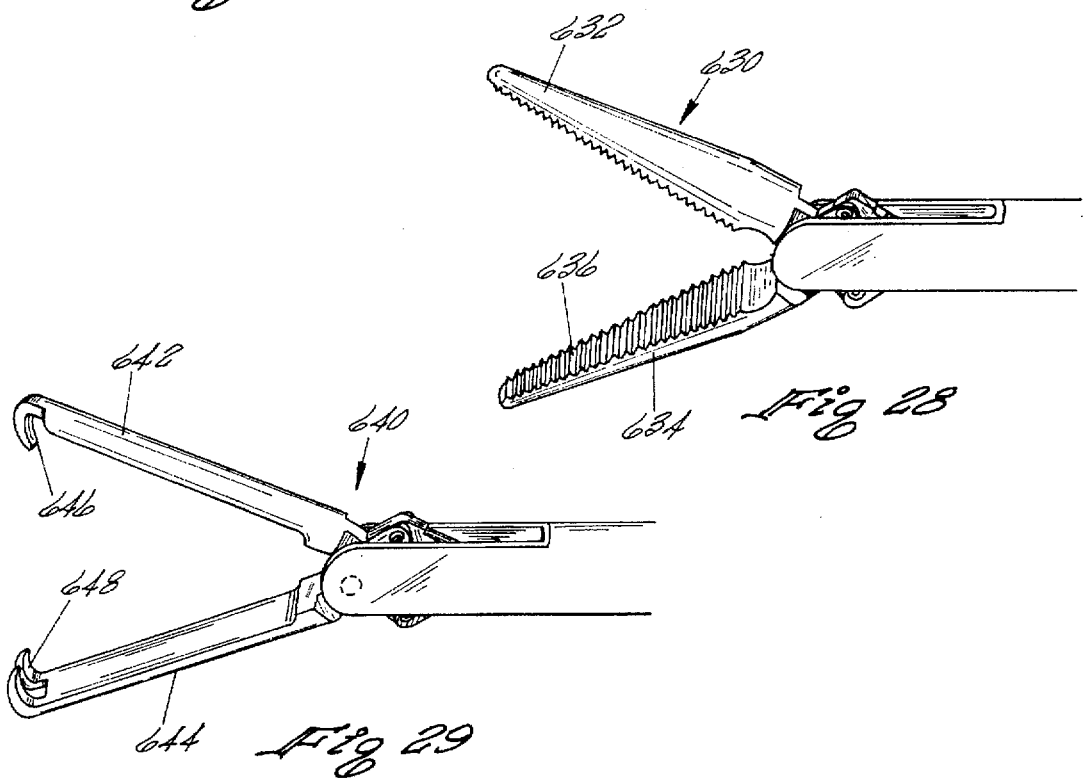

SURGICAL INSTRUMENT WITH REMOVABLE SHAFT ASSEMBLY

BACKGROUND OF THE INVENTION

1. Field of the Invention

This invention relates generally to surgical instruments for use in performing medical procedures and specifically, to surgical instruments for use in performing minimally invasive surgical procedures. Minimally invasive procedures may be performed using trocars, cannulas, laparoscopes and specially designed surgical instruments. The surgical instruments of the present invention include reusable shaft assemblies which are designed to be used for a predetermined number of surgical procedures. The surgical instrument includes a permanent handle assembly which is used with the reusable shaft assemblies.

2. Description of the Prior Art

Surgical instruments for performing medical surgery are well known in the art. Historically, medical surgeries have been performed using what is referred to as "open procedures." In an "open procedure," the surgeon typically makes a large incision in the vicinity of the operative site, performs the necessary procedure and then closes the wound. Typically, the wound is closed using sutures or other closing type devices, such as surgical staples. An example of an "open procedure" is the removal of the gall bladder.

Over the last several years, micro-surgery has developed using endoscopic techniques. These procedures are generally referred to as "minimally invasive surgery." The use of minimally invasive surgery has several attendant advantages, such as, for example, reduced medical costs, reduced hospital stays, and most importantly, reduced patent trauma.

Specialized instrumentation has been developed to facilitate minimally invasive surgeries. These specialized instruments include, for example, specialized endoscopes referred to as laparoscopes, trocars, cannulas and related instrumentation.

Surgeons performing minimally invasive surgeries require specifically designed surgical instruments which are dimensioned to pass through cannulas and laparoscopes. Such instruments include a wide variety of tip structures such as scissors, graspers, needle holders and the like. Further, certain of the surgical instruments can be utilized with electrosurgical generators to perform tissue cutting and tissue and blood coagulation.

Certain of the specialized instrumentation being developed are considered to be "disposable instruments" which are designed for single use only. Typically, such disposable instruments are packed in individual containers, are sterilized and are labelled for "single use."

As a result of the trend of the health care field using "disposable instruments," and disposable supplies in a procedure, the costs of medical procedures have been increasing. The results are that each surgical procedure uses a large number of disposable supplies and disposable instruments.

One result of this trend is that insurers are starting to place limits on the amount of disposable supplies and disposable instruments that can be used in a surgical procedure as a means of controlling costs to be reimbursed to the health care providers by the insurance carrier. Other problems that have developed relate to environmental concerns, such as, for example, disposal of medical waste.

Thus, the medical field has progressed from using totally reusable instruments, such as a scalpel, as was originally used in open procedures, to use of totally reusable instruments for minimally invasive surgery. Typical of reusable instruments designed for minimally invasive surgery is a surgical instrument disclosed in U.S. Pat. No. 4,674,501.

U.S. Pat. No. 4,674,501 discloses a surgical scissor-like assembly having a pair of axially mating and relatively slidable elongated shafts each provided with a handle. The surgical instrument includes an articulation interconnector by which the shafts are simultaneously reciprocable relative to each other and conjointly moveable about their common axis. Working tool member are provided at the end of each shaft. An indexing wheel is provided to rotate the elongated shafts including the scissor-like assembly.

A protective mechanism for surgical rongeur is disclosed by U.S. Pat. No. 5,009,661. Rongeurs are surgical instrument designed to bite off and hold fragments of tissue. The rongeur disclosed in U.S. Pat. No. 5,009,661 comprises an integral instrument having a safety spring mechanism interposed between an activating means, such as the handle, and a drive mechanism for closing the jaws for the purpose of protecting the instrument from failure due to peak stress overload of the jaws.

Several U.S. patents disclose surgical instruments that are designed to be easily assembled and disassembled to facilitate cleaning and sterilization.

U.S. Pat. No. 5,308,358 discloses rigid-shaft surgical instruments that can be disassembled for improved cleaning.

U.S. Pat. Nos. 4,122,856 and 4,084,584 disclose a surgical instrument having grasping or cutting jaw assembly at a distal end and a proximal end portion detachably connected to a handle assembly. The structure of the handle provides for quick coupling of this instrument and handle assembly.

U.S. Pat. No. 3,894,336 discloses a suture removal scissor having attached thereto semi-rigid flexible handle means. The handle means are fictionally and removeably attached to the scissors.

U.S. Pat. No. 3,777,538 discloses a surgical tip applicator comprising an elongated barrel removeably mounted to a pistol grip actuator handle with the actuator jaws acting cooperatively at the distal end of the barrel.

U.S. Pat. No. 2,113,246 discloses an endoscopic forceps wherein a removable instrument assembly having a scissor or forceps at the distal end of a conduit has a rear portion which cooperates with a handle having a saddle which functions as a means for interengaging with the rear portion to hold the instrument assembly rigidly within the handle. The saddle includes a hinged cover to enclose the rear portion during use and which can be opened to separate the handle from the instrument. Also, certain of the instruments are designed to be entirely disposable after use for single procedure or to have tip assemblies which are disposable.

U.S. Pat. No. 5,282,800 discloses a surgical instrument consisting of a disposable working member and a reusable handle member. The reusable handle member, preferably, comprises a hinged barrel adapted to receive the working member.

U.S. Pat. Nos. 5,308,358 and 4,590,936 each utilize a handle having a slot which cooperates with a connecting member to hold the same wherein the slot is located at the proximal end of a shaft forming part of the instrument sub-assembly.

CIRCON ACMI Division of Circon Corporation offers for sale a line of surgical instruments having a universal handle, Catalog No. 330H, that is interchangeable with scissor or forceps stems, Catalog No. Series 330, 311 and 332. Their universal handle and interchange stems were designed to be reusable for surgery and requires appropriate disinfecting, cleaning and sterilizing between medical procedures. Such interchange handle and stems were designed for use with rigid cystoscopes and resectoscopes.

Typical of surgical instruments adapted for use in minimally invasive surgery procedures with electrosurgical generators is a polyspectome snare with bipolar electrode disclosed in U.S. Pat. No. 4,905,691. Electrosurgical instruments which are designed for use with monopolar or bipolar electrosurgical generators are likewise known in the art.

In addition to the above described structure of surgical instruments, U.S. Pat. No. 5,293,878 discloses a stepped rotatable end actuator which enables rotation of the end effectors such as grasping tool, relative to the handle assembly to overcome the necessity of rotating the handle assembly.

U.S. Pat. No. 5,314,424 discloses a surgical instrument locking mechanism such as a trigger, a brake and a latch spring, which directly co-acts with a tool mechanism for releaseably positioning and locking a tool mechanism in position.

SUMMARY OF THE INVENTION

The present invention discloses a novel, unique and improved surgical instrument which is adapted for use in surgical procedures. In the preferred embodiment, the surgical instrument is used in minimally invasive procedures.

The surgical instrument includes a shaft assembly and a handle assembly. The shaft assembly includes a drive shaft having a first end and a second end. The first end has an actuatable working member and the second end has a connecting member. The drive shaft has formed thereon, at a predetermined location near said first end, a reaction member having a preselected geometrical shape. The reaction member is adapted to removeably operatively connect with a receiving member forming a reacting support. A driving force applied to the drive shaft reacts with the reacting support to develop a reaction force to actuate the actuated working member in a predetermined direction.

The surgical instrument handle assembly includes an elongated hollowed out housing for removeably supporting the shaft assembly. The elongated housing has a first end which defines the receiving member to removeably operatively connect with the reaction member defining a reaction support. The elongated housing has a second end which terminates in an opening enabling the drive shaft to pass therethrough to position the connecting member a selected distance beyond the opening. The handle assembly includes a releasable coupling member which releasably connects with the connecting member.

The prior art reusable surgical devices require cleaning, disinfecting and sterilizing between procedures. The design of the prior art instruments generally do not lend themselves to easy cleaning resulting in tissue or other matter remaining in the shaft or other mechanical parts of the surgical instruments. The assemblies of U.S. Pat. Nos. 5,308,358, 4,122, 856, 4,084,594 and 3,777,538 require the surgical staff in an operating room to disassemble the instrument for cleaning and sterilization and to then reassemble the instrument prior to surgery. Such activities are time consuming and require that the user be trained and knowledgeable in assembling the disassembled instruments.

With the concern of infectious disease, hepatitis B and potential of cross-contamination to patients and health care professionals, the known surgical instruments are difficult to clean and require extraordinary cleaning process to insure that the same are free from foreign material.

Another problem associated with prior art surgical instruments is that continued use of the actuatable working member, such as, for example, a scissor, tends to dull the cutting edges requiring resharpening or other processing of the actuatable working member in order to enable reliable reuse of the surgical instrument in surgical procedure.

The known prior art surgical instruments are generally designed with a predetermined handle grip design which limits the choice of handle grips available to a surgeon.

Certain of the known prior art surgical instruments having a rotary member, such as, for example, the surgical instrument of U.S. Pat. No. 4,674,501 are lacking a means for inhibit rotation of shaft assembly during activation of the actuatable working element. Further, the stepped rotatable end actuator disclosed in U.S. Pat. No. 5,293,878 is complicated and requires that user to step through a plurality of discrete dent positions.

The locking mechanism of U.S. Pat. No. 5,314,424 is a multi-part assembly and requires that movement, such as applying a proximal force to a trigger.

Although the primary advantage of disposable, one time use of surgical instruments is to reduce the risk of cross-contamination, the high cost per instrument and the environmental problems associated with medical waste disposed are becoming significant limitation factors in promoting use of laparoscope surgical instruments.

The surgical instrument if the present invention overcomes certain of the disadvantages of the prior art surgical instruments.

One advantage of the surgical instruments of the present invention is that a handle assembly having an elongated housing can be used with interchangeable shaft assemblies wherein the interchangeable shaft assemblies having a number of tip assemblies.

Another advantage of the present invention is that the surgical instrument shaft assembly includes a reaction member which removeably operatively connects to a reaction member located distally in a handle assembly to form a reaction support. The reaction support concurrently provides a positive connecting assembly for insuring that the removeably shaft assembly will not separate from the handle assembly during a surgical procedure.

Another advantage of the present invention is that the handle assembly includes a pivotable handle grip whereby pivoting of the handle grip produces a reaction force at the reaction support to actuate the actuatable working member located at the distal tip of the shaft assembly.

Another advantage of the present invention is that the handle assembly includes a slot having a rotatable cap assembly which locks and captures an extended connecting member located at the end of the shaft assembly and the connecting member in the slot to provide redundant fastening a rotatable cap which locks with the reaction member and receiving member connecting assembly.

Another advantage of the present invention is that the surgical instrument includes a rotary member which the surgeon can rotate with a single finger. By rotating the rotary member, the surgeon can rotate the elongated housing, drive shaft and tip assembly during a procedure.

Another advantage of the present invention is that the rotary member includes a locking member which, upon pivoting of the handle grip in a direction to actuate the working member, the handle assembly concurrently locks the rotary member to inhibit rotation during activation of the actuatable member.

Another advantage of the present invention is that the shaft assemblies, having different actuatable working members, or tips, and handle assemblies, are interchangeable.

Another advantage of the present invention is that the surgical instruments can be easily disassembled for cleaning and sterilizing and cleaning access to all instrument areas is provided.

Another advantage of the present invention is that the design of the surgical instrument facilitates easy and rapid instrument disassembly and reassembly.

Another advantage of the present invention is that the handle assembly includes a rotatable cap assembly having a protrusion finger-like member to preclude inadvertent tip release. Further, the instrument includes insulated handles and shafts for electrosurgical procedures and an automatic shaft rotation brake which engages as tissue is grasped.

Another advantage of the present invention is that the handle assemblies and shaft assemblies may be insulated for use with an electrosurgical generator. For example, the surgical instruments can be used with monopolar cautery. The shaft assemblies could have a variety of actuatable working elements such as, for example, scissors, dissecting forceps and biopsy forceps.

Another advantage of the present invention is that the shaft assemblies can be designed to have a wide variety of actuatable working elements including dissecting forceps, biopsy forceps, scissors, needle holders and grasping forceps.

BRIEF DESCRIPTION OF THE DRAWINGS

These and other advantages of the invention will be readily apparent when considered in light of the detailed description hereinafter of the preferred embodiment and of the drawings which include the following figures:

FIG. 1 is a top, front and right side perspective view of a surgical instrument having a handle assembly and a removable shaft assembly;

FIG. 2 is a top, front and left side perspective view of the surgical instrument of FIG. 1;

FIG. 3 is a front elevational view of the surgical instrument of FIG. 1;

FIG. 4 is a right end elevational view of the proximal end of the surgical instrument of FIG. 3;

FIG. 5 is a left end elevational view of the distal end of the surgical instrument in FIG. 3;

FIG. 6 is a top view of the surgical instrument of FIG. 3;

FIG. 7 is a bottom view of the surgical instrument of FIG. 3;

FIG. 12 is a partial front view, partially in cross-section showing the connecting member located at the proximal end of the shaft assembly prior to locking and capture by the slotted cap assembly;

FIG. 13(a) is a top, front and left side perspective view of the slotted cap assembly having the cap member rotatable to permit the connecting member located at the proximal end of the shaft assembly to be placed into the slot;

FIG. 13(b) is a top, front and left side perspective view of the slotted cap assembly having the cap member rotated to place the protrusion finger-like member in position and to inhibit removal of the connecting member from the slot;

FIGS. 14(a), 14(b) and 14(c) are top partial cross-sectional pictorial views illustrating the step of directing the connecting member into the slot, locking the connection member in the slot and rotating the cap member to capture the connecting member in the slot, respectively;

FIGS. 15(a), 15(b) and 15(c) are top, partial cross-sectional views illustrating the same steps shown by FIGS. 14(a), 14(b) and 14(c), respectively;

FIGS. 16(a), 16(b) and 16(c) are partial front views showing a reaction member located in a drive shaft prior to loading, the reaction member being loaded into the receiving member located distally on the elongated hollowed out housing of the handle assembly, and the reaction member being removeably operatively connected to the receiving member, respectively;

FIG. 17 is a partial front view of another embodiment of a reaction member and receiving member structure to form a reacting support;

FIG. 18 is a top, front and left side perspective view of another embodiment of this invention;

FIGS. 19(a) and 19(b) are partial cross-sectional views illustrating another embodiment of a rotational braking or locking means showing the rotational mode and braking mode, respectively;

FIGS. 25 through 29 illustrate various species for the actuatable working element.

DESCRIPTION OF THE PREFERRED EMBODIMENT

Figure 8:
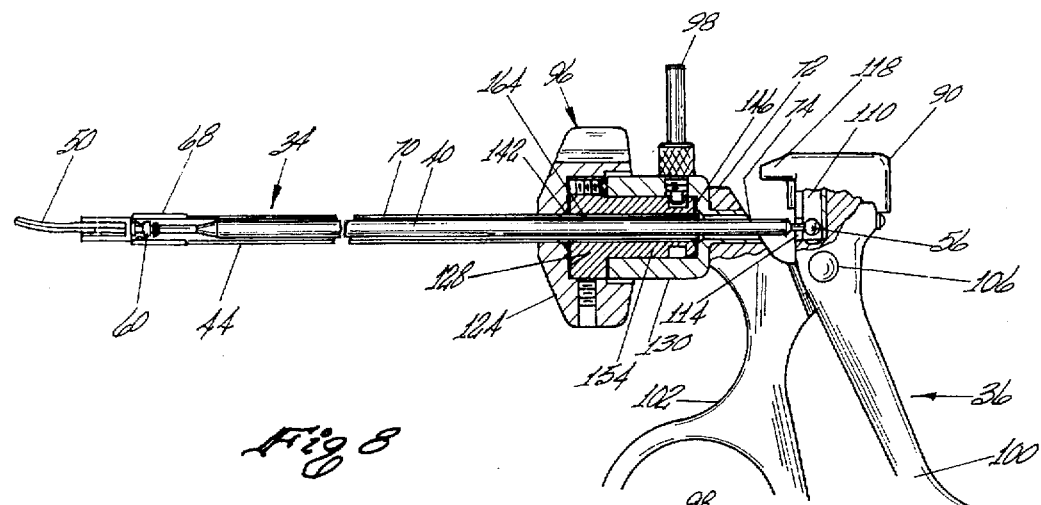
FIGS. 8 and 9 are partial front elevational views, partially in cross-section, showing the braking or locking mechanism and slot and cap assembly structure for locking and capturing the connecting member at the proximal end of a shaft.

The surgical instrument described herein in the preferred embodiment comprises a permanent handle assembly which can be utilized with shaft assemblies that are designed for a limited number of uses, and therefore, after such limited number of uses are to be disposed. Thus, by practicing the teachings of this invention, the surgical instrument utilizes the advantages of both fully reusable and disposable surgical instruments. However, it is also envisioned that the unique structure of the shaft assemblies could be likewise used in reusable instrument shaft assemblies, where beneficial. Therefore, the description of the preferred embodiment is of a surgical instrument that is semi-reusable which has results in significant reduction of instrumentation cost of surgery and affords the costs of the semi-reusable shaft assemblies amortized over several patents reducing patient cost.

In FIGS. 1 through 7, the surgical instrument is shown generally as 30 has a shaft assembly shown generally as 34 (the shaft of which is enclosed by an elongated hollowed-out housing of the handle assembly as described herein) and a handle assembly shown as 36.

The shaft assembly 34 has a drive shaft 40 having a first end 44 and a second end 46. The first end 40 has an actuatable working member such as a scissor having blades 50.

The second end 46 terminates in a connecting member 56 which may be in the form of a spherical or ball member. The structure of the preferred embodiment of the connecting member is illustrated in greater detail in FIGS. 14(a), 14(b) and 14 (c).

The drive shaft 40 has formed thereon at a predetermined location near the first end 44 a reaction member 60. The structure of the preferred embodiment of the reaction member 60 is illustrated in greater detail in FIGS. 16(a), 16(b) and 16(c). The reaction member 60 is adapted to removeably operatively connect with a receiving member 68 located at the proximal end of an elongated hollowed-out housing 70 of the handle assembly. The reaction member 60 and the receiving member 68 form a reacting support whereby a driving force applied to the drive shaft 40 reacts with the reacting support to develop a reaction force to actuate the actuatable working member 50.

The handle assembly 36 supports the elongated hollowed-out housing 70 which has a first end which defines the receiving member 68. The handle assembly 36 functions to removeably support the shaft assembly 34.

The elongated housing 70 has a second end 72 in the form of a handle support which terminates in an opening 74 enabling the drive shaft 40 to pass therethrough to position the connecting member 56 a selected distance beyond the opening 74. The handle assembly 36 includes a releasably coupling member, such as, for example, a rotatable cap assembly 90 which releaseably connects with the connecting member 56.

A locking rotational member shown generally as 96 is provided to enable the user to rotate the elongated housing 70 and shaft assembly 34 to position the actuatable working member 50 at a desired angle at the operative site without having to rotate the handle assembly 36. Once in position, the user merely squeezes the handle and locks the rotatable member 96 in position. The rotary member 96 has a central axis which is co-axial with the axis of the elongated housing 70.

The elongated housing 70 may be insulated to enable the instrument to be used with a monopolar R.F. electrosurgical generator. One example of an insulating covering may be TEFLON® material. An electrosurgical connector 98 is provided which applies an R.F. signal to the shaft assembly 34.

Figure 9:
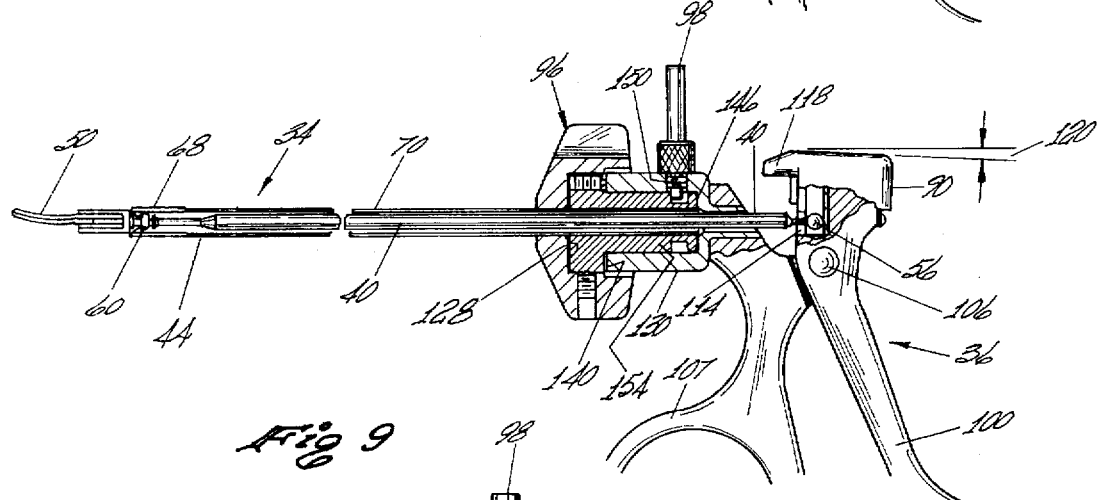

FIGS. 8 and 9 illustrate the details of the structure of the instrument. The handle assembly 36 includes a pair of handles 100 and 102 which are pivotally mounted on a pin 106. The upper section of handle 100 includes a slot 110 which has an opening 114 for receiving, passing and locking the connecting member 56.

Figure 9A:
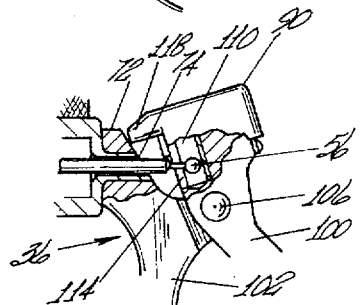
FIG. 9(a) is a partial front view showing the protrusion finger-like member which inhibits inadvertent release of the shaft assembly from the handle assembly.

The cap assembly 90 includes a cover having a protruding finger-like member 118 extending therefrom. The length of the protruding finger-like member is selected to prevent the cap assembly 90 from contacting handle support 72 as illustrated in FIG. 9(a).

FIG. 8 illustrates the shaft assembly 34 being loaded or inserted into the handle assembly 36. The shaft 40 passes through the elongated housing 70 causing the connecting member 56 to pass through the opening 114 and into slot 110. The cap assembly 90 is turned 90° clockwise during the loading or insertion stage. Upon completion of loading or insertion, the cap assembly 90 is rotated 90° counter clockwise placing the protruding finger-like member 114 in the position shown in FIG. 8.

The reaction member 60 of the shaft assembly 34 is seated in the receiving member 68 forming the reaction support.

As illustrated in FIG. 9, the user squeezes handles 100 and 102 causing the handle 100 to pivot relative to pin 106 causing the cap assembly to deflect through a small actuate angle shown by 120. This movement applies a drive force on shaft 40 which applies the drive force to the reaction support. The drive force is applied to reaction member 60 which develop a reaction force to actuate the working member, e.g. scissor 50, in a predetermined manner, for example, to cut tissue.

Handle 102 has an upper section which supports the locking rotational member 96 and its assorted components. The rotational locking member 96 includes a rotary member 124 having a central axis and a central opening 128 which extends along the central axis and which encloses a tube connector 130 operatively connected to the elongated housing 70. The tube connector 130 has an interior chamber 134 which extends axially therethrough from a first entry opening 140 to second aligned support opening 146 spaced from and coaxially aligned with the first entry opening 140. The tube connector 130 has an entry port 150 thereon adjacent the second aligned opening 146.

Figure 10:
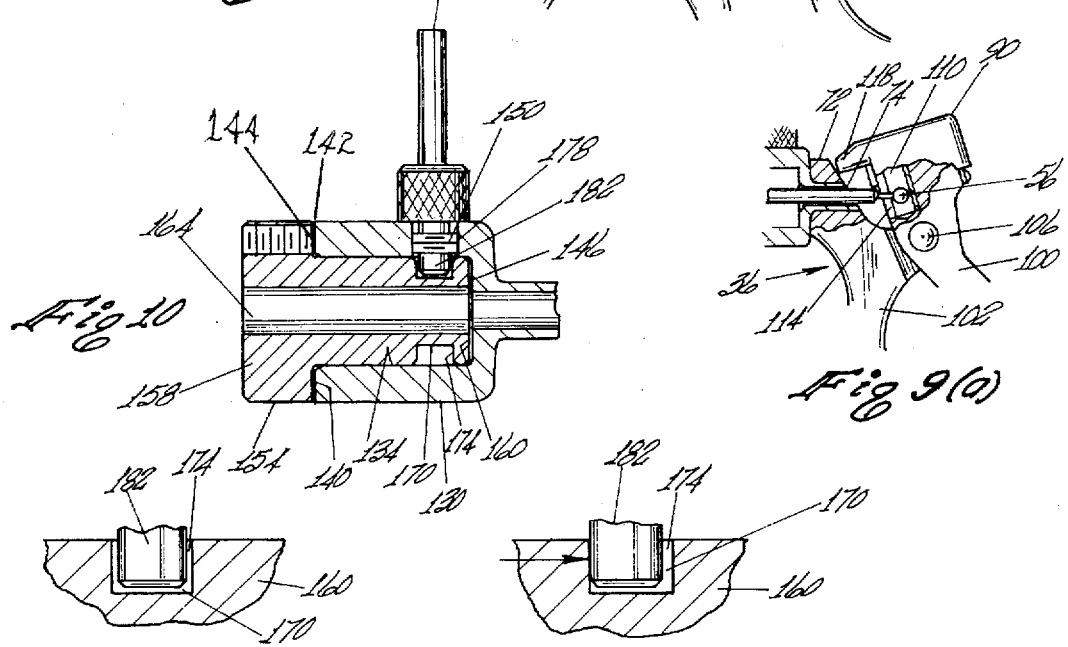
FIG. 10 is a partial cross-sectional view illustrating the structural details of the rotary member, tube connector, central hub and locking element.

Referring now to FIG. 10, a central hub 154 has a first section 158, a second section 160 and an aperture 164 extending axially therebetween. The central hub 154 encloses and is operationally attached to the exterior surface of the elongated housing 70 as illustrated in FIGS. 9 and 10. Also, as illustrated in FIG. 10, a sectored disk 142 is located around the first entry opening of the tubular connector 130. An engagement member shown as part of central hub 158 is positioned to slideably engage the sectored disk to position rotationally the rotary member at one of the selected diskette radial positions shown as 144.

The central hub 154 has an annular shaped slot 170 with sidewalls 174 extending circumferentially around the second section 160. The central hub 154 is positioned with the first section 158 within the central opening 128 of the rotary member 124. The second section 160 is located within the interior chamber 134 of the tube connector 130. The central hub 154 is operatively attached to the rotary member 124 such that when the rotary member 124 is rotated about its central axis, the rotary member 124 rotates the elongated housing 70 and the shaft assembly 34 supported therein.

Figure 11A:
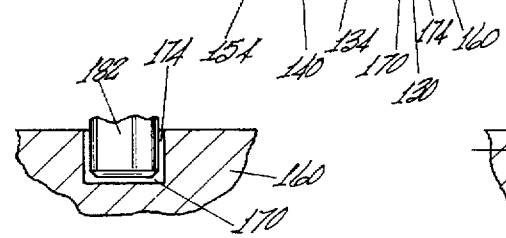
FIG. 11(a) illustrates the position of the projected end of the locking element within an annular shaped slot within the central hub to permit rotation of the rotary member.
Figure 11B:
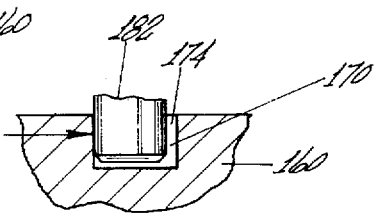
FIG. 11(b) illustrates the position of the projected end of the locking element being urged against the side walls of the annular slot to inhibit rotation of the rotary member.

FIGS. 10, 11(a) and 11(b) show the details of the electrosurgical connector 98 which has located at an end thereof a locking element 178. As shown in FIG. 10, the electrosurgical connector 98 having the locking element 178 is rigidly mounted within the entry port 150. The locking element 178 defines a projected end 182 as shown in FIGS. 11(a) and 11(b) which is positioned with the projected end 182 extending into communication with the annular shaped slot 170 formed in second section 160 of the central hub 154.

FIG. 11(a) illustrates that the projected end 182 cooperates with the side walls 174 of the annular slot 170 to permit rotation of the elongated housing 70 (shown in FIG. 8 and FIG. 9) with rotation of the rotating member 124 in the absence of a driving force being applied to the drive shaft 40 by the handle assembly 36.

FIG. 11(b) illustrates that the projected end 182 is urged against and into tight contact with the side walls 174 of the annular slot 170 to inhibit rotation of the elongated housing 70 and the shaft assembly 34 when a drive force is applied to the drive shaft to actuate an actuatable working element.

FIG. 12 illustrates the position of the connecting member 56 during the loading or insertion of the shaft 40 into the cap assembly 90 which occurs before the rotation thereof to the captured position shown in FIG. 8

FIGS. 13(a), 13(b), 14(a) through 14(c) and 15(a) through 15(c) illustrates pictorially the locking and capturing of the connecting member 56 within the slot 110. The connecting member 56 is located at the end of the shaft 40.

Specifically, in order to pass the connecting member 56 of shaft 40 through the opening 114 into the slot 110, the cap assembly 90 is rotated 90° clockwise placing the protruding finger-like member 118 away from the shaft 40. This moves lip 180 [shown in FIG. 15(c)] away from the opening 114. During insertion, the shaft 40 is pushed axially within the elongated housing 70 urging the connecting member 56 into and locked within the slot 110. The cap assembly 90 is then turned counter clockwise 90° as shown in FIG. 13(b) to capture the connecting member 56 within the slot 110.

FIGS. 14(a), 14(b) and 14(c) illustrate sequentially the steps of directing the connecting member 56 into slot 110, locking the connecting member 56 in slot 110 and rotating the cap assembly 90 to capture the connecting member, respectively.

FIGS. 15(a) 15(d) and 15(c) illustrate pictorially the position of the handle 100 to tilt the cap assembly 90 to receive, lock and capture the connecting member 56 within the slot 110. FIG. 15(c) shows that when the cap assembly 90 is rotated 90° to capture the connecting member 56, a moving lip 180 blocks the opening 114 to prevent inadvertent separation of the shaft assembly 34 from the handle assembly 36 during use. To separate the shaft assembly 36, the cap assembly 90 must be rotated clockwise 90° and the handle 100 and 102 are pushed apart which pushes the receiving member 60 out of the receiving member 68.

FIGS. 16(a), 16(b) and 16(c) illustrate the step of loading or inserting of the shaft assembly 34 into the elongated housing 20.

FIG. 16(a) shows that when the shaft 40 is inserted into the elongated housing 70, the reaction member 60 adjacent the working element member 50 is positioned adjacent the receiving member 68 located at the distal end of the elongated housing 70.

FIG. 16(b) illustrates that the reaction member 60 is urged against the receiving member 68 which, in the preferred embodiment, is in the form of a split spring like member. FIG. 16(c) illustrates that when the handle assembly 36 is squeezed as discussed in connection with FIG. 9, a compression force is applied between the reaction member 60 and the receiving member 68 snapping the reaction member 60 into the spring like member of the receiving member 68 forming a reacting support or fixed support to activate the actuatable working member in response to a drive force. When the handle assembly 36 is further squeezed to move or linearly translate the shaft 40 in a first direction, the force developed at the reacting support or fixed support is applied directly to the jaws 50. Further movement of the shaft as the handle assembly is squeezed pushes the jaws 50 into the open position. As illustrated in FIGS. 25 through 29, discussed below, either one or both of the jaws can be opened depending on the structure of the jaws. Likewise as illustrated in FIG. 1, when the handle assembly 36 is moved to an unsqueezed position, the movement of the shaft 40 in a direction opposite to the first direction pulls the jaws 50 into a closed position. As illustrated in FIGS. 16(a), 16(b) and 16(c), the reaction member 60 is in the form of a circumferential ring structure.

FIG. 17 illustrates an alternative embodiment of a reaction member 260 in the form of raised boss which is located adjacent an actuatable working member 250 and near the distal end of shaft 240. The elongated housing 270 includes a receiving member 268 which is adapted to receive the reaction member 260.

FIG. 18 illustrates another embodiment of a surgical instrument 300 having a handle assembly 336 having a ratcheted handle and a shaft assembly 334 which is locked and captured by a cap assembly 290. The actuatable working member is shown as 350. The rotational and rotating mechanism 396 operates differently than the preferred embodiment shown in FIGS. 1 through 9.

FIGS. 19(a) and 19(b) illustrate the structural details of the rotational and locking mechanism 396 having an unlocking or rotational position, FIG. 19(a) and a locking or non-rotational position FIG. 19(b).

In FIGS. 19(a) and 19(b), a tubular connector 398 is operatively connected to the handle assembly 336 and has a slot 404 formed therein. A hub 410 located within the tubular connector 398 has a slot 412 formed therein. The rotational member 314 has a pair of spring loaded latching members 418 and 420 which are adapted to co-act with slots 412 and 404 respectively.

When the rotational member 314 is positioned as shown in FIG. 19(a) with the latching member 420 located at the proximal end of slot 404, the rotational member along with elongated housing and drive shaft assembly can be rotated by the user. Latching member 420 rides over the edge of the slot 404 permitting rotation.

FIG. 19(b) illustrates that slot 404 has a projected end or locking key 424 located distally in the slot 404. When the rotational member 394 is moved toward the distal end of the surgical instrument, the latching member 418 slides in slot 412 and the latching member 420 slides forward and engages the protruding end or locking key 424 which inhibits rotation.

Figure 20:
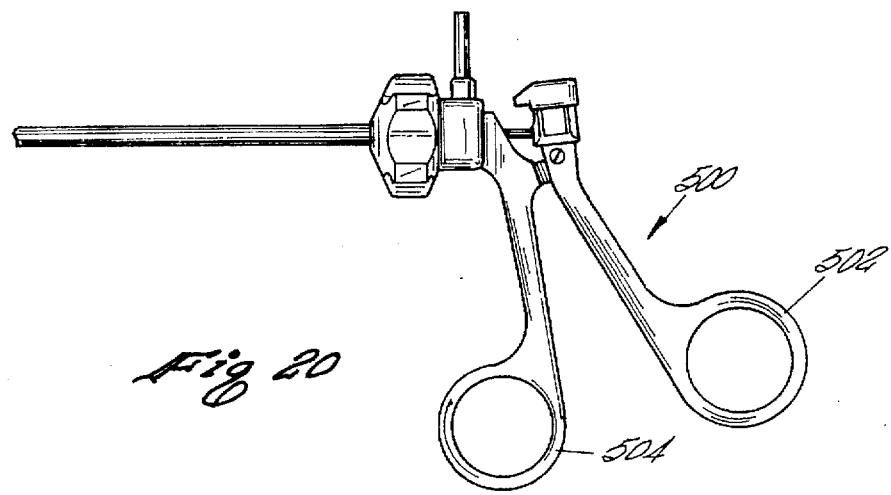
FIGS. 20 through 24 illustrate various embodiments of the handle assembly.

FIG. 20 illustrates one embodiment of a handle assembly 500 having handles in the form of single rings 502 and 504 which are insulated.

Figure 21:
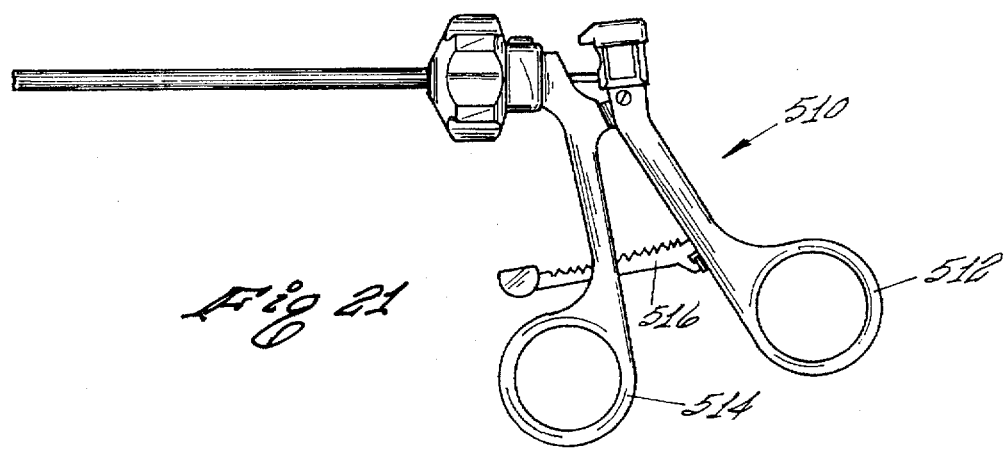

FIG. 21 illustrates another embodiment of a handle assembly 510 having handles in the form of single rings 512 and 514 and ratcheted member 516 wherein the handles are non-insulated.

Figure 22:
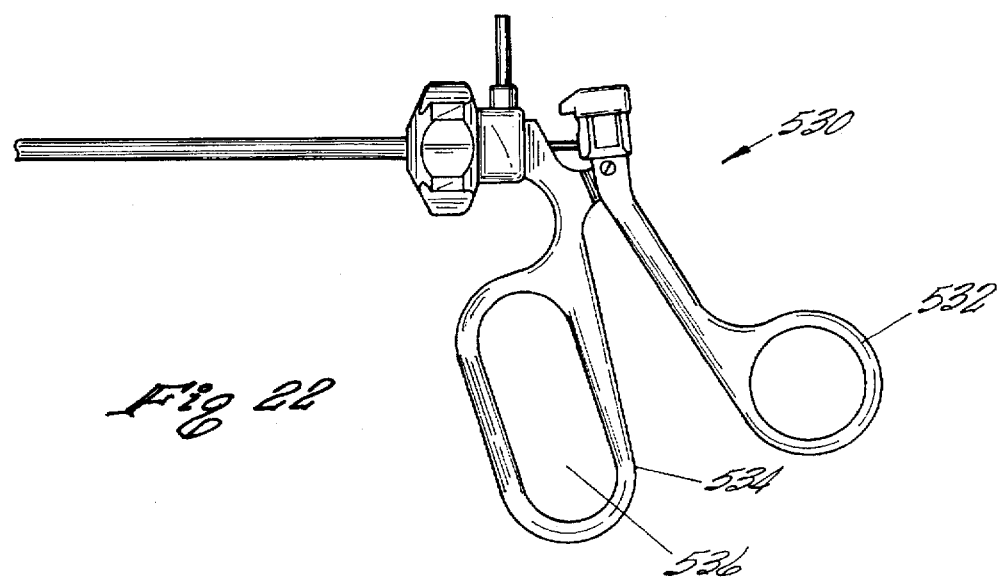

FIG. 22 illustrates another embodiment of a handle assembly 530 having handles wherein one handle is in the form of a single ring 532 and the other handle is in the form of a double ring 534 wherein the double ring 534 has an opening 536 to receive at multiple fingers of a user. The handles are insulated.

Figure 23:
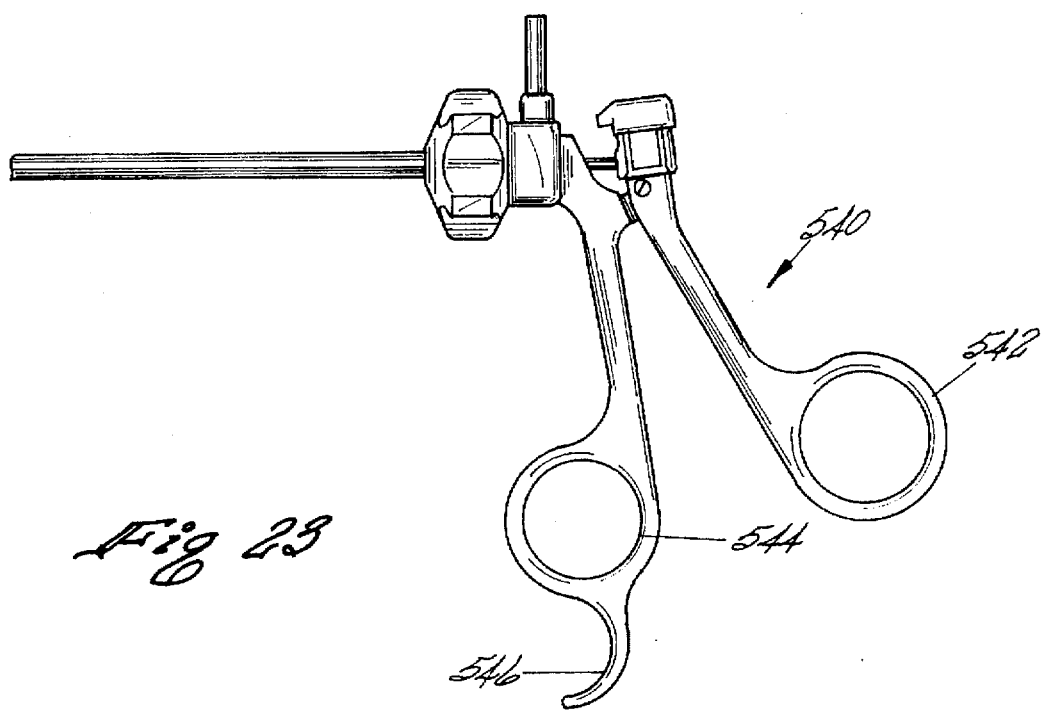

FIG. 23 illustrates another embodiment of a handle assembly 540 having handles in the form of single rings 542 and 544 wherein ring 544 has a finger tang. The handles are insulated.

Figure 24:
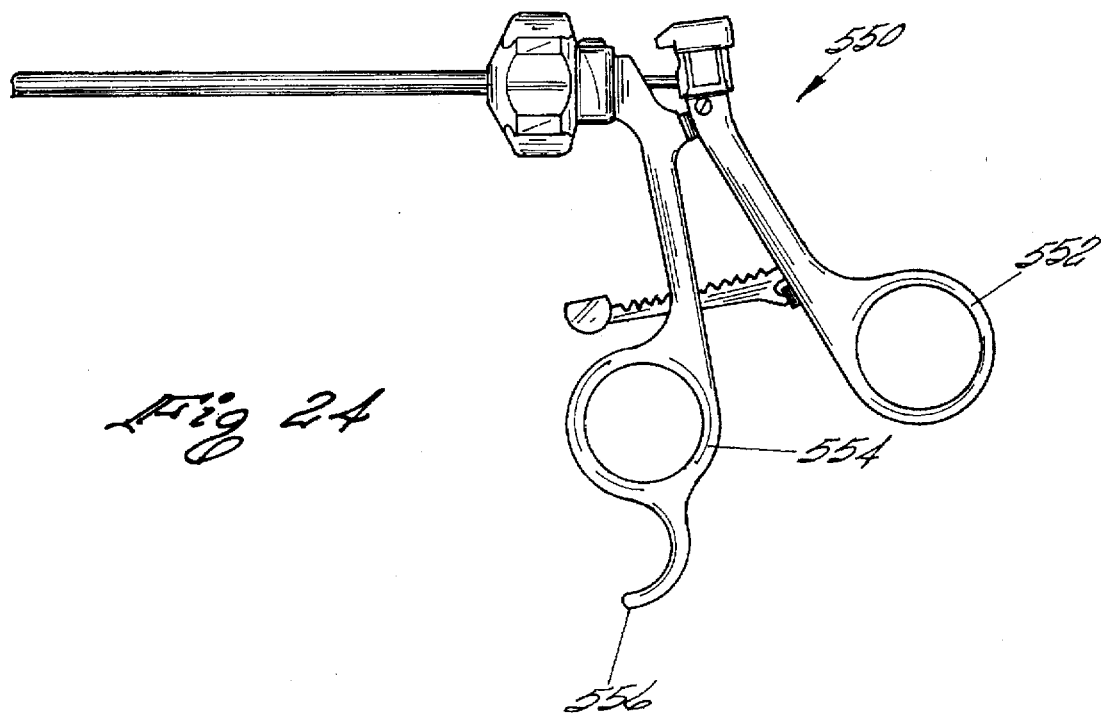

FIG. 24 illustrates another embodiment of a handles assembly 550 having handles in the form of single rings 552 and 554 wherein ring 554 has a finger tang 556. This structure includes a ratcheted member. The handles are non-insulated.

FIGS. 25 through 29 illustrate various embodiments of tips which could be used as an actuatable working element.

FIG. 25 illustrates a cross-serrated needle holder 600 having an upper jaw 602 and a lower jaw 604. Lower jaw 604 is shown having cross-serrations 606 which likewise are formed on the upper jaw 602. The cross-serrated needle holder may be formed of tungsten carbide knurled jaws for grasping needles.

FIG. 26 illustrates a hook scissor 610 having an upper blade or jaw 612 and a lower blade or jaw 614 wherein jaw 614 has a shearing surface 616 formed thereon. The hook scissor 610 is a single action scissor for isolating tissue and precise cutting.

FIG. 27 illustrates a biopsy forceps 620 having an upper jaw 622 and a lower jaw 624 each formed into oval cupped jaws wherein the lower jaw has an opening 626. The biopsy forceps 620 is a single action working element member having oval cupped jaws for tissue biopsy.

FIG. 28 illustrates a needle nose dissecting forceps 63 having a long, thin, tapered, serrated upper jaw 632 and lower jaw 634 wherein the lower jaw 634 has a serrated surface 636. The upper jaw 632 has a similar surface. The needle nose dissecting forceps 630 has a long, thin, tapered, serrated upper jaws which are ideal for precise dissection.

FIG. 29 illustrates a claw grasping forceps 640 having an upper jaw 642 and a lower haw 644. The upper jaw 646 has a single tooth 646 while the lower jaw has two teeth 648. The claw grasping forceps 640 has durable teeth on the jaw for traumatic grasping of thick-walled tissue.

The description of the preferred embodiment set forth herein is not intended to limit the teaching of the present invention and are exemplary. The teachings herein have wide applications to surgical instruments for use in minimally invasive surgery and for other than for minimally invasive surgery. For example, surgical instruments utilizing the teachings of this invention can be used for open procedure or in specialized procedures such as thoracoscopy, OB/GYN procedures and other specialized surgical procedures.

What is claimed is:

1. A surgical instrument shaft assembly comprising
a drive shaft having a first end, a second end and an insulating covering to prevent an electrosurgical current from passing from the drive shaft, said first end having an actuatable working member and said second end having a connecting member, said drive shaft having formed thereon at a predetermined location near said first end a reaction member in the form of a raised boss member, said reaction member being adapted to removeably operatively connect with a receiving member in the form of a split spring like member located on an elongated housing extending from a handle assembly forming a reacting support whereby a driving force applied to the drive shaft reacts with said reacting support to develop a reaction force to actuate said actuated working member in a predetermined direction.

2. The surgical instrument of claim 1 wherein said actuatable working member is a dissecting forceps.

3. The surgical instrument of claim 1 wherein said actuatable working member is a biopsy forceps.

4. The surgical instrument of claim 1 wherein said actuatable working member is a scissor.

5. The surgical instrument of claim 1 wherein said actuatable working member is a needle holder.

6. The surgical instrument of claim 1 wherein said actuatable working member is a grasping forceps.

7. The surgical instrument shaft assembly of claim 1 wherein said raised boss member has a preselected width.

8. The surgical instrument shaft assembly of claim 1 wherein said connecting member is in the form of an extended protrusion.

9. The surgical instrument shaft assembly of claim 1 wherein said connecting member is in the form of a sphere.

10. A surgical instrument comprising
a shaft assembly comprising
a drive shaft having a first end and a second end, said first end having an actuatable working member and said second end having a connecting member, said drive shaft having formed thereon at a predetermined location near said first end a reaction member in the form of a raised boss member, said reaction member being adapted to removeably operatively connect with a receiving member in the form of a split spring like member located on an elongated housing extending from a handle assembly forming a reacting support whereby a driving force applied to the drive shaft reacts with said reacting support to develop a reaction force to actuate said actuated working member in a predetermined direction; and
a handle assembly including an elongated hollowed-out housing for removeably supporting said shaft assembly, said elongated housing having a first end which defines a split spring like receiving member which receives and is urged slightly apart by said raised boss member to removeably connect with said raised boss member of said reaction member defining a reaction support, said elongated housing having a second end which terminates in an opening enabling said drive shaft to pass therethrough to position said connecting member a selected distance beyond said opening, said handle assembly including a releasable coupling member which releasably connects with said connecting member.

11. The surgical instrument of claim 10 wherein said releaseable coupling member is a rotatable cap assembly.

12. The surgical instrument of claim 10 wherein said handle assembly includes a pair of handle rings.

13. The surgical instrument of claim 12 wherein said handle rings have an insulating covering to prevent an electrosurgical current from passing from the handle rings.

14. The surgical instrument of claim 10 wherein said handle assembly comprises
a pivotable handle grip whereby pivoting of said handle grip moves said drive shaft producing a reaction force at said reaction support.

15. The surgical instrument of claim 14 wherein said pivotable handle grip includes a first handle ring and a second handle ring.

16. The surgical instrument of claim 15 wherein said first handle ring is operatively coupled to said elongated housing and said second handle ring is operatively connected to and movable relative to said first handle ring.

17. The surgical instrument of claim 16 wherein said second handle ring has said releasable coupling member located therein and positioned to receive and releasably connect to the connecting member located on said drive shaft.

18. The surgical instrument of claim 17 wherein said first handle ring includes a single ring for gripping by a single finger of a user.

19. The surgical instrument of claim 18 wherein said single ring further includes a finger tang for gripping by a second finger of a user.

20. The surgical instrument of claim 17 wherein said first handle ring includes a double ring for multiple finger insertion of a user.

21. The surgical instrument of claim 14 wherein said pivotable handle grip can be moved in a first direction transporting said drive shaft within said elongated housing in said first direction to generate a reaction force at said reaction support to actuate said actuatable member in a first selected direction and wherein said handle grip can be moved in a second direction opposite to said first direction transporting said drive shaft within said elongated housing in a second direction to generate a reaction force at said reaction source to actuate said actuatable member in a second selected direction.

22. The surgical instrument of claim 21 wherein said pivotable handle grip is further pivoted in said second direction to develop at said reaction support a separation force having sufficient magnitude for urging the reaction member and shaft assembly away and separating from said receiving member wherein said releasable coupling member is disconnected from said connecting member and said receiving member returns to its original position from its slightly apart position.

23. A surgical instrument handle assembly comprising
   an elongated hollowed-out housing for removeably supporting a drive shaft of a surgical instrument shaft assembly, said elongated housing having a first end which defines a split spring like receiving member to be urged slightly apart by and removeably operatively connect with a reaction member on a drive shaft;
   a handle assembly operatively connected to said elongated housing whereby movement of said handle is adapted to transport said drive shaft; and
   a releasable coupling member positioned at a selected location on said handle assembly, said releasable coupling member being adapted to releasably connect with a connecting member on a drive shaft.

24. The surgical instrument handle assembly of claim 23 wherein said releasable coupling member includes
   a hollowed-out member having an opening adapted to receive a connector member on a drive shaft; and
   a locking member adapted to lock a connector member within said hollowed-out member.

25. A surgical instrument comprising
   a shaft assembly comprising
      a drive shaft having a first end and a second end, said first end having an actuatable working member and said second end having a connecting member, said drive shaft having formed thereon at a predetermined location near said first end a reaction member having a preselected geometrical shape, said reaction member being adapted to removeably operatively connect with a receiving member located on an elongated housing extending from a handle assembly forming a reacting support whereby a driving force applied to the drive shaft reacts with said reacting support to develop a reaction force to actuate said actuated working member in a predetermined direction; and
   a handle assembly including an elongated hollowed-out housing for removeably supporting said shaft assembly, said elongated housing having a first end which defines a spring like receiving member to be slightly urged apart by and to removeably connect with said reaction member defining a reaction support, said elongated housing having a second end which terminates in an opening enabling said drive shaft to pass therethrough to position said connecting member a selected distance beyond said opening, said handle assembly including a releasable coupling member which releasably connects with said connecting member, said releasable coupling member being a rotatable cap assembly.

26. The surgical instrument of claim 25 wherein said actuatable working member is a dissecting forceps.

27. The surgical instrument of claim 25 wherein said actuatable working member is a biopsy forceps.

28. The surgical instrument of claim 25 wherein said actuatable working member is a scissor.

29. The surgical instrument of claim 25 wherein said actuatable working member is a needle holder.

30. The surgical instrument of claim 25 wherein said actuatable working member is a grasping forceps.

31. The surgical instrument of claim 25 wherein said drive shaft has an insulating covering to prevent an electrosurgical current from passing from said drive shaft.

32. The surgical instrument shaft assembly of claim 25 wherein said reaction member is in the form of raised boss member having a preselected width and said receiving member is in the form of a cooperating split spring like member.

33. The surgical instrument shaft assembly of claim 25 wherein said connecting member is in the form of an extended protrusion.

34. The surgical instrument shaft assembly of claim 25 wherein said connecting member is in the form of a sphere.

35. A surgical instrument comprising
   a shaft assembly comprising
      a drive shaft having a first end and a second end, said first end having an actuatable working member and said second end having a connecting member, said drive shaft having formed thereon at a predetermined location near said first end a circumferential ring reaction member having a preselected geometrical shape, said reaction member being adapted to removeably operatively connect with a receiving member located on an elongated housing extending from a handle assembly forming a reacting support whereby a driving force applied to the drive shaft reacts with said reacting support to develop a reaction force to actuate said actuated working member in a predetermined direction; and
   a handle assembly including an elongated hollowed-out housing for removeably supporting said shaft assembly and a pivotable handle grip adapted to move said drive shaft producing a reaction force at said reaction support, said elongated housing having a first end which defines a receiving member to be slightly urged apart by and to removeably connect with said reaction member defining a reaction support, said elongated housing having a second end which terminates in an opening enabling said drive shaft to pass therethrough to position said connecting member a selected distance beyond said opening, said handle assembly including a releasable coupling member which releasably connects with said connecting member a pivotable handle grip whereby pivoting of said pivotable handle grip in a first direction moves said drive shaft in a first direction producing a reaction force at said reaction support and pivoting of said handle in said second direction to develop at said reaction support a separation force having sufficient magnitude for urging the reaction member and shaft assembly away and separating from said receiving member wherein the releasable coupling member is disconnected from said connecting member.

36. The surgical instrument of claim 35 wherein said releasable coupling member is a rotatable cap assembly.

37. The surgical instrument of claim 35 wherein said handle assembly includes a pair of handle rings.

38. The surgical instrument of claim 37 wherein said handle rings have an insulating covering to prevent an electrosurgical current from passing from the handle rings.

39. The surgical instrument of claim 38 wherein said pivotable handle grip includes a first handle ring and a second handle ring.

40. The surgical instrument of claim 39 wherein said first handle ring is operatively coupled to said elongated housing and said second handle ring is operatively connected to and movable relative to said first handle ring.

41. The surgical instrument of claim 40 wherein said second handle ring has said releasable coupling member located therein and positioned to receive and releasably connect to said connecting member located on said drive shaft.

42. The surgical instrument of claim 41 wherein said first handle ring includes a single ring for gripping by a single finger of a user.

43. The surgical instrument of claim 42 wherein said single ring further includes a finger tang for gripping by a second finger of a user.

44. The surgical instrument of claim 41 wherein said first handle ring includes a double ring for multiple finger insertion of a user.

45. The surgical instrument of claim 35 wherein said pivotable handle grip can be moved in a first direction transporting said drive shaft within said elongated housing in said first direction to generate a reaction force at said reaction support to actuate said actuatable member in a first selected direction and wherein said handle grip can be moved in a second direction opposite to said first direction transporting said drive shaft within said elongated housing in a second direction to generate a reaction force at said reaction source to actuate said actuatable member in a second selected direction.

46. The surgical instrument of claim 35 wherein and said pivotable handle grip is further pivoted in said second direction to develop at said reaction support a separation force having sufficient magnitude for urging the reaction member and shaft assembly away and separating from said receiving member wherein said releasable coupling member is disconnected from said connecting member.

47. A surgical instrument handle assembly comprising an elongated hollowed-out housing for removeably supporting a drive shaft of a surgical instrument shaft assembly, said elongated housing having a first end which defines a split spring like receiving member to be slightly urged apart by and to removeably operatively connect with a reaction member on a drive shaft;

a handle assembly operatively connected to said elongated housing whereby movement of said handle is adapted to transport a drive shaft;

a releasable coupling member positioned at a selected location on said handle assembly, said releasable coupling member including
  a hollowed-out member having an opening adapted to receive a connector member on a drive shaft; and
  a locking member adapted to lock a connector member within said hollowed-out member;

said releasable coupling member being adapted to releasably connect with a connecting member on a drive shaft.

* * * * *